United States Patent
Roy et al.

[11] Patent Number: 6,143,856
[45] Date of Patent: Nov. 7, 2000

[54] PROCESS FOR THE PRODUCTION OF PHENOLIC-RICH PYROLYSIS OILS FOR USE IN MAKING PHENOL-FORMALDEHYDE RESOLE RESINS

[75] Inventors: Christian Roy, Sillery; Xiao Lu, Ste.Foy; Hooshang Pakdel, Neufchâtel, all of Canada

[73] Assignee: Pyrovac Technologies Inc., Sainte-Foy, Canada

[21] Appl. No.: 09/244,783

[22] Filed: Feb. 5, 1999

[51] Int. Cl.[7] .............................. C08G 8/04; C08G 14/04
[52] U.S. Cl. ........................ 528/129; 528/1; 528/16; 528/497; 528/509 C; 524/13; 524/72; 524/73; 524/74; 524/735; 568/727; 203/40; 203/42; 203/46
[58] Field of Search ................ 528/129, 502 C, 528/497, 1, 86; 524/13, 72, 73, 74, 735; 568/727; 203/40, 42, 46

[56] References Cited

U.S. PATENT DOCUMENTS

| 4,233,465 | 11/1980 | Gallivan et al. |
|---|---|---|
| 4,962,269 | 10/1990 | Chum et al. |
| 5,034,498 | 7/1991 | Himmelblau ............... 528/230 |
| 5,115,084 | 5/1992 | Himmelblau ............... 528/230 |

*Primary Examiner*—Duc Truong
*Attorney, Agent, or Firm*—Foley & Lardner

[57] ABSTRACT

A phenolic-rich pyrolysis oil is produced by pyrolysing lignocellulosic material at a temperature of no more than about 550° C under an absolute pressure of no more than about 50 kPa to produce pyrolysis vapors, and condensing the pyrolysis vapors to obtain a condensate consisting of a phenolic-rich pyrolysis oil having a dew point of about 65 to about 75° C. under an absolute pressure of about 15 to about 20 kPa. Such a phenolic-rich pyrolysis can be directly used in making phenol-formaldehyde resol resins.

26 Claims, 1 Drawing Sheet

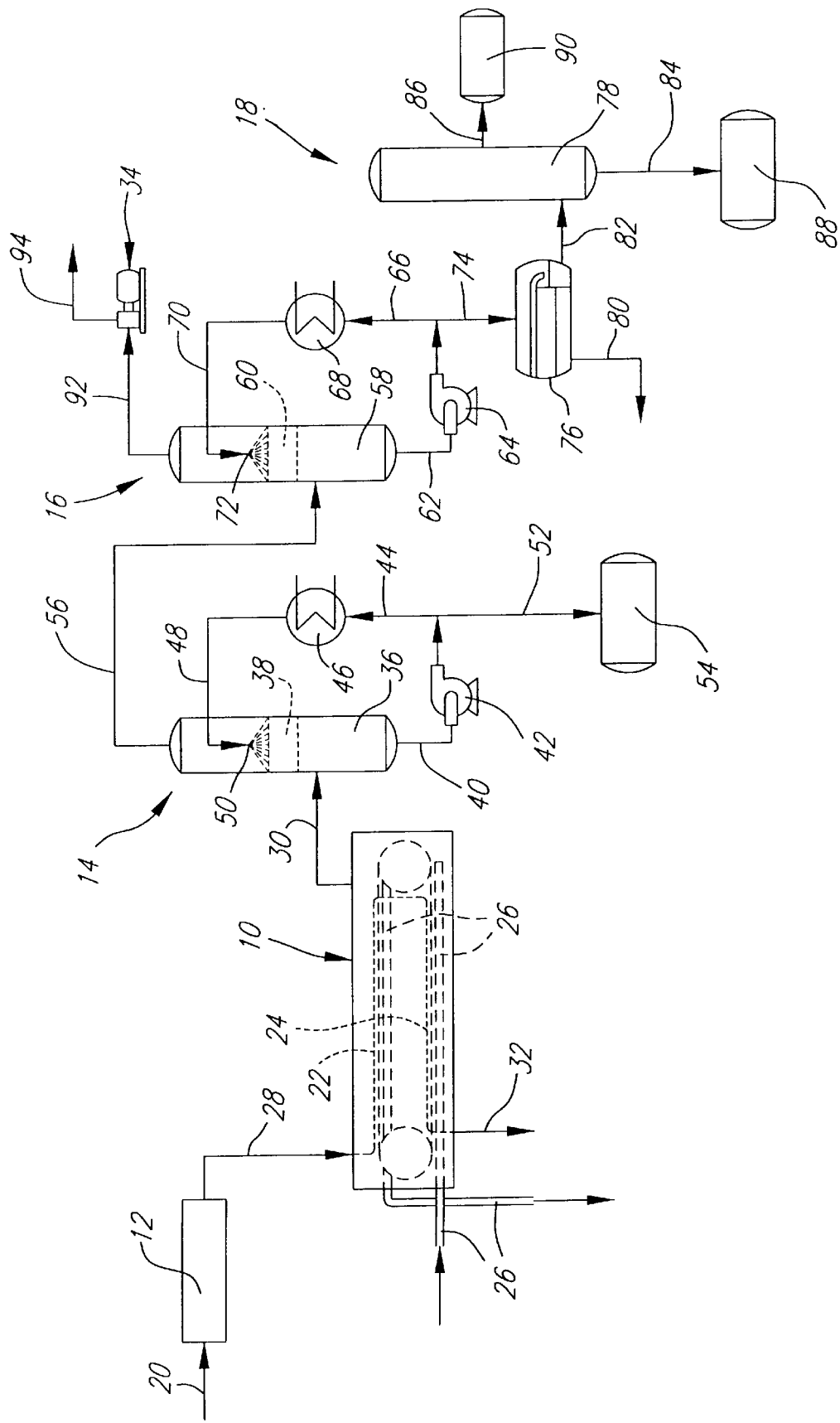

PROCESS FOR THE PRODUCTION OF PHENOLIC-RICH PYROLYSIS OILS FOR USE IN MAKING PHENOL-FORMALDEHYDE RESOLE RESINS

BACKGROUND OF THE INVENTION

The present invention relates to a process for the production of phenolic-rich pyrolysis oils suitable for use in making phenol-formaldehyde resol resins. More particularly, the invention is directed to the production of phenolic-rich pyrolysis oils from lignocellulosic materials.

Phenol-formaldehyde or phenolic resins are typically cross-linkable polymeric resins. There are two types of phenolic resins; both types are made from phenol and aldehydes, usually pure phenol and formaldehyde. One type of phenolic resin, novolak, is made under acidic conditions using excess phenol; the acid catalyzes the reaction of phenol and formaldehyde to form the cross-linkable polymeric resin. Novolak resins are used for the formation of molded pieces and articles. The other type of phenolic resin, resol, is made under basic conditions using excess formaldehyde; a small amount of a base is added to the phenol to catalyze the reaction thereof with formaldehyde and form the cross-linkable polymeric resin. Resol resins are used as adhesives for gluing together the veneer plies of exterior-grade plywood panels and the flakes of oriented strand board panels. The cured adhesive is resistant to moisture, preventing delamination of the panels.

Because phenol is produced primarily from petroleum, its price and availability are linked to that of petroleum. Consequently, phenolic resins are relatively expensive. A number of attempts have thus been made in recent years to at least partially substitute the petroleum-based phenol in phenolic resins with inexpensive phenols derived from lignocellulosic wastes such as bark, sawdust, wood chips and the like.

The pyrolysis of lignocellulosic materials is known to produce a complex mixture of phenolic compounds which are derived primarily from the lignin contained in the feedstock. Such a complex mixture of phenolic compounds requires expensive fractionation in order to provide a phenolic fraction which can be used as a substitute for the petroleum-based phenol in the synthesis of phenolic resins. For example, in an attempt to formulate new adhesives for wood, Chum and Black have proposed in U.S. Pat. No. 4,962,269 a process for fractionating fast-pyrolysis oils derived from lignocellulosic materials to produce a phenolic compounds/neutrals fraction. The process involves a series of liquid-liquid extraction steps, wherein the phenolic compounds partitioned in an organic phase from the pyrolysis oil phase and the organic phase is then treated with an aqueous alkali metal bicarbonate solution. The complexity and lengthy solvent extraction associated with a relatively low yield of the phenolic compounds/neutrals fraction limit the industrial applications of such a process. The same disadvantages are encountered in the fractionation process described in U.S. Pat. No. 4,233,465.

SUMMARY OF THE INVENTION

It is therefore an object of the present invention to overcome the above drawbacks and to provide a process for the production of phenolic-rich pyrolysis oils which can be directly used for making phenol-formaldehyde resol resins.

According to one aspect of the invention, there is provided a process for the production of a phenolic-rich pyrolysis oil, which comprises the steps of:
  a) pyrolysing lignocellulosic material at a temperature of no more than about 550° C. under an absolute pressure of no more than about 50 kPa to produce pyrolysis vapors; and
  b) condensing the pyrolysis vapors to obtain a condensate consisting of a phenolic-rich pyrolysis oil having a dew point of about 65 to about 750° C. under an absolute pressure of about 15 to about 20 kPa.

Applicant has found quite unexpectedly that by condensing pyrolysis vapors derived from lignocellulosic material at a temperature ranging from about 65 to about 750° C and an absolute pressure ranging from about 15 to about 20 kPa, or at equivalent temperature/pressure thermodynamic conditions, one obtains a condensate consisting of a phenolic-rich pyrolysis oil which is capable of functioning as efficiently as petroleum-based phenols in the production of phenol-formaldehyde resol resins. Such a phenolic-rich pyrolysis oil can thus be directly used in making phenol-formaldehyde resol resins.

The present invention therefore provides, in another aspect thereof, a phenolic-rich pyrolysis oil derived from lignocellulosic material and having a dew point of about 65 to about 750° C. under an absolute pressure of about 15 to about 20 kPa.

According to a further aspect of the invention, there is also provided a method of preparing phenol-formaldehyde resol resins, which comprises substituting a phenolic-rich pyrolysis oil as defined above for a portion of phenol in a phenol-formaldehyde resol composition.

According to still another aspect of the invention, there is provided a phenol-formaldehyde resol resin containing a phenolic-rich pyrolysis oil as defined above.

The lignocellulosic material used as feedstock advantageously comprises bark waste, preferably softwood bark waste, since such a feedstock enables one to obtain pyrolysis oils having high contents of phenolic compounds. Examples of suitable softwoods include fir, pine, spruce, larch and mixtures thereof. The bark waste is preferably in the form of particles having a particle size of about 15 to about 25 mm in order to ensure optimum heat transfer.

According to a preferred embodiment, step (a) is carried out at a temperature of about 400 to about 550° C. and an absolute pressure of about 10 to about 50 kPa. Care should be taken to not exceed a temperature of about 550° C. and a pressure of about 50 kPa, since extensive secondary cracking of the pyrolysis vapors occurs at temperatures and pressures above 550° C. and 50 kPa, respectively. Preferably, the pyrolysis is carried out at a temperature of about 475° C. and a pressure of about 15 to about 20 kPa to provide the desired phenolic-rich pyrolysis oil in an optimum yield while reducing extensive secondary cracking of the pyrolysis vapors.

As previously indicated, step (b) is carried out at a temperature ranging from about 65 to about 75° C. and an absolute pressure ranging from about 15 to about 20 kPa, or at equivalent temperature/pressure thermodynamic conditions. Operating within such temperature and pressure ranges enables one to avoid condensing water vapor, carboxylic compounds of low molecular weight such as acetic and formic acids and undesirable odorous compounds of low molecular weight, which occurs at temperatures below 65° C., and also to avoid polymerization reactions and the formation of highly viscous liquids, which occur at temperatures above 75° C. Preferably, step (b) is carried out to obtain a phenolic-rich pyrolysis oil having a dew point of about 68–70° C. under an absolute pressure of about 15 to about 20 kPa. The phenolic-rich pyrolysis oil which is obtained in step (b) has been found to contain about 70 wt. % of phenolic compounds such as monophenols, polyphenols, flavanoids, low-molecular-weight lignins and tannins, about 19 wt. % of neutral compounds such as ketones, aldehydes, steroids and furfural derivatives, and about 11 wt. % of sugars such as levoglucosane and high molecular weight carboxylic acids such as fatty acids.

According to another preferred embodiment, non-condensed pyrolysis vapors obtained in step (b) are further condensed at a temperature of no more than about 45° C., preferably at about 15–30° C., and an absolute pressure of about 15 to about 20 kPa, or at equivalent temperature/pressure thermodynamic conditions, to obtain a further condensate comprising an organic phase in admixture with an aqueous phase. Since the organic phase contains desirable phenolic compounds which were not condensed in step (b), it is preferably separated from the aqueous phase and the separated organic phase is subjected to an evaporation so as to recover a residue comprising a phenolic fraction boiling above 125° C. under atmospheric pressure. Such a phenolic fraction can be mixed with the aforesaid phenolic-rich pyrolysis oil for use in making phenol-formaldehyde resol resins.

Since the phenolic-rich pyrolysis oil and/or the phenolic fraction boiling above 125° C. under atmospheric pressure may contain high molecular weight carboxylic acids in quantities which inhibit the reaction of such oil and/or fraction with formaldehyde in the production of phenol-formaldehyde resol resins, the phenolic-rich pyrolysis oil and/or phenolic fraction can be purified by extraction with an organic solvent selected from the group consisting of $C_5$–$C_8$ saturated hydrocarbons and petroleum ether to obtain a first fraction comprising phenolic oil with a minor portion of the high molecular weight carboxylic acids and a second fraction comprising the organic solvent and a major portion of the high molecular weight carboxylic acids dissolved therein, the first and second fractions being immiscible with one another, separating the first and second fractions from one another and recovering the first fraction. Preferably, the organic solvent utilized is hexane.

The above purification method is also useful for removing hydrocarbons which may be present in the phenolic-rich pyrolysis oil and/or phenolic fraction and which are inert in the reaction of such oil and/or fraction with formaldehyde, but which have a diluting effect.

The present invention therefore provides, in another aspect thereof, a method of purifying a phenolic-rich pyrolysis oil containing high molecular weight carboxylic acids, which comprises the steps of:

a) extracting the oil with an organic solvent selected from the group consisting of $C_5$–$C_8$ saturated hydrocarbons and petroleum ether to obtain a first fraction comprising a phenolic oil with a minor portion of the high molecular weight carboxylic acids and a second fraction comprising the organic solvent and a major portion of the high molecular weight carboxylic acids dissolved therein, the first and second fractions being immiscible with one another;

b) separating the first and second fractions from one another; and c) recovering the first fraction.

BRIEF DESCRIPTION OF THE DRAWINGS

Further features and advantages of the invention will become more readily apparent from the following description of preferred embodiments, with reference to the accompanying drawings in which the single FIGURE is a schematic illustration of a vacuum pyrolysis plant for treating lignocellulosic material to produce a phenolic-rich pyrolysis oil, according to the invention.

DESCRIPTION OF PREFERRED EMBODIMENTS

The vacuum pyrolysis plant illustrated comprises a double-tray reactor 10 for pyrolysing under vacuum softwood bark waste, a pre-treatment unit 12 for pre-treating the bark waste prior to being fed to the reactor 10, primary and secondary condenser units 14 and 16 for condensing the pyrolysis vapors generated in the reactor 10 and a fractionation unit 18 for recovering a phenolic fraction from the condensate discharged from the secondary condenser unit 16. The unit 12 includes a grinder for reducing coarse bark waste fed via line 20 into particles having a particle size of about 15–25 mm and a dryer for drying the particles to a moisture content of about 10–15 wt. %.

The reactor 10 is a horizontal moving bed reactor of the type described in copending U.S. patent application Ser. No. 08/811,172 filed Mar. 4, 1997, the teaching of which is incorporated herein by reference. The reator 10 includes two trays 22,24 arranged one above the other and heated by means of molten salt circulating through conduit 26 in contact with the trays 22 and 24. The bark particles which are fed via line 28 to the reactor 10 fall onto the upper tray 22 on which they are conveyed along one direction by a conveyor system (not shown) and then fall onto the lower tray 24 on which they are conveyed in the opposite direction, while being heated at a temperature of about 400–550° C. by the molten salt circulating in the conduit 26. The reactor 10 is provided with a discharge outlet 30 for discharging the non-condensable gases and condensable vapors generated in the reactor and a discharge outlet 32 for discharging the solid carbonaceous material formed therein. The discharge outlet 30 is connected via the primary and secondary condenser units 14 and 16 to a vacuum pump 34 for maintaining an absolute pressure of about 15 to about 20 kPa in the reactor 10.

The gases and vapors discharged from the reactor 10 through the outlet 30 are sent to the primary condenser unit 14. The condenser unit 14 comprises a packed bed tower 36 containing a packing 38 of Raschigs rings onto which are sprayed fine oil droplets having a temperature of about 65 to about 75° C., obtained by recirculating a portion of the oil condensed in the tower 36 via line 40, pump 42, line 44, heat exchanger 46 where the oil is cooled to a temperature of 65–75° C. and then via line 48 to spray nozzle 50. As the gases and vapors ascend the tower 36 and pass through the packing 38 of Raschigs rings, they encounter the cooled oil droplets sprayed by the nozzle 50, resulting in the condensation of the vapors having a dew point of about 65–75° C. under the operating subatmospheric pressure conditions, thereby obtaining a substantially water-free phenolic-rich pyrolysis oil which accumulates at the bottom of the tower 36. The portion of the phenolic-rich pyrolysis oil which is not recirculated is sent via line 52 to the storage tank 54.

The non-condensable gases and non-condensed vapors comprising water vapor, carboxylic compounds of relatively low molecular weight, phenolic compounds of relatively low molecular weight and undesirable odorous compounds of low molecular weight leaving the tower 36 are sent via line 56 to the secondary condenser unit 16. The condenser unit 16 is similar to the unit 14, but operates at a lower temperature, e.g. about 15 to about 30° C. The unit 16 comprises a packed bed tower 58 containing a packing 60 of Raschigs rings onto which are sprayed fine droplets of condensate having a temperature of 15–30° C., obtained by recirculating a portion of the condensate formed in the tower 58 via line 62, pump 64, line 66, heat exchanger 68 where the condensate is cooled to a temperature of 15–30° C. and then via line 70 to spray nozzle 72. The condensate formed in the tower 16 comprises an organic phase in admixture with an aqueous phase, the organic phase containing the phenolic compounds of low molecular weight. The portion of the condensate which is not recirculated is sent via line 74 to the fractionation unit 18 comprising a decanter 76 and an evaporation tower 78 for recovering the phenolic compounds contained in the organic phase.

In the decanter 76, the organic phase and aqueous phase are separated from one another by decantation. The separated aqueous phase is sent via line 80 to a water treatment unit (not shown), whereas the organic phase obtained is sent via line 82 to the evaporation tower 78, where it is subjected to an evaporation. The tower 78 includes a bottom outlet 84 for discharging a residue comprising a phenolic fraction boiling above 125° C. under atmospheric pressure, and a lateral outlet 86 for discharging the fraction boiling at a temperature less than 125° C. The phenolic fraction which contains phenolic compounds of relatively low molecular weight is sent to the storage tank 88 and is advantageously mixed with the phenolic-rich pyrolysis oil contained in the tank 54 for use in making phenol-formaldehyde resol resins. The other fraction having a boiling point below 125° C. is sent to the storage tank 90.

The non-condensable gases leaving the tower 58 are sent via line 92, vacuum pump 34 and line 94 to combustion utilities (not shown).

The following non-limiting examples further illustrate the invention.

EXAMPLE 1

A feedstock comprising 194.5 kg of softwood bark waste having a moisture content of 6.5 wt. % and consisting of 70 vol. % fir, 28 vol. % spruce and 2 vol. % larch was pyrolyzed in reactor 10 at a temperature of 468° C. under an absolute pressure of 18.9 kPa. The pyrolysis vapors were condensed in tower 36 at a temperature of 71° C. under the same pressure. 53.27 kg of a phenolic-rich pyrolysis oil were obtained, representing a yield of 29.37% on anhydrous wood basis.

Non-condensed vapors leaving the tower 36 were condensed in tower 58 at a temperature of 27° C. under an absolute pressure of 18.9 kPa, to obtain 38.07 kg of a condensate comprising an organic phase in admixture with an aqueous phase. The organic and aqueous phases were separated from one another in decanter 76 and the separated organic phase (7.82 kg) was subjected to an evaporation in tower 78. 5.44 kg of a phenolic fraction boiling above 125° C. under atmospheric pressure were recovered, representing a yield of 2.96% on anhydrous wood basis.

The phenolic fraction boiling above 125° C. and discharged from the tower 78 was combined with the phenolic-rich pyrolysis oil discharged from the tower 36. The combined oils were subjected to chemical analysis. The results are shown in Table I:

TABLE 1

| Compound type | Wt. % | Molecular weight distribution |
|---|---|---|
| Hydrocarbons | 3 | $200 < M_w < 300$ |
| Sugars | 9 | $M_w < 300$ |
| Acids | 1.5 | $M_w < 100$ |
| Fatty acids | 10 | $150 < M_w < 300$ |
| Alcohols (linear) | 1 | $M_w < 250$ |
| Esters | 1 | $M_w < 250$ |
| Phenols | 10 | $100 < M_w < 250$ |
| Ketones | 2 | $M_w < 250$ |
| Hydroxy ketones | 1 | $M_w < 250$ |
| Cyclic alcohols | 1.5 | $M_w < 250$ |
| Steroids | 2 | $350 < M_w < 450$ |
| Triterpenoids | 2 | $350 < M_w < 450$ |
| Flavonoids | 18 | $280 < M_w < 400$ |
| Tannins and Derivatives | 25 | $380 < M_w < 500$ |
| Polyphenols and Polyflavonoids | 5 | $M_w > 500$ |
| Labile compounds | 8 | N.D. (2) |
| Total | 100 | |

(1) approximate values (moisture and ash-free basis)
(2) N.D. = non determined.

As it is apparent from the above Table, the phenols, flavonoids, tannins, polyphenols and polyflavonoids which constitute phenolic compounds represent 58 wt. % of the total weight of the oil composition.

EXAMPLE 2

A feedstock comprising 205.25 kg of softwood bark waste having a moisture content of 6.5 wt. % and consisting of 70 vol. % fir, 28 vol. % spruce and 2 vol. % larch was pyrolyzed in reactor 10 at a temperature of 400° C. under an absolute pressure of 18.7 kPa. The pyrolysis vapors were condensed in tower 36 at a temperature of 70° C. under the same pressure. 50.71 kg of a phenolic-rich pyrolysis oil were obtained, representing a yield of 26.49 % on anhydrous wood basis.

Non-condensed vapors leaving the tower 36 were condensed in tower 58 at a temperature of 35° C. under an absolute pressure of 18.7 kPa, to obtain 45.44 kg of a condensate comprising an organic phase in admixture with an aqueous phase. The organic and aqueous phases were separated from one another in decanter 76 and the separated organic phase (10.19 kg) was subjected to an evaporation in tower 78. 7.09 kg of a phenolic fraction boiling above 125° C. under atmospheric pressure were recovered, representing a yield of 3.69% on anhydrous wood basis.

EXAMPLE 3

A feedstock comprising 205.32 kg of softwood bark waste having a moisture content of 11.7 wt. % and consisting of 70 vol. % fir, 28 vol. % spruce and 2 vol. % larch was pyrolyzed in reactor 10 at a temperature of 483° C. under an absolute pressure of 16.7 kPa. The w pyrolysis vapors were condensed in tower 36 at a temperature of 68° C. under the same pressure. 39.85 kg of a phenolic-rich pyrolysis oil were obtained, representing a yield of 21.98% on anhydrous wood basis.

Non-condensed vapors leaving the tower 36 were condensed in tower 58 at a temperature of 43° C. under an absolute pressure of 16.7 kPa, to obtain 45.59 kg of a condensate comprising an organic phase in admixture with an aqueous phase. The organic and aqueous phases were separated from one another in decanter 76 and the separated organic phase (13.63 kg) was subjected to an evaporation in tower 78. 9.81 kg of a phenolic fraction boiling above 125° C. under atmospheric pressure were recovered, representing a yield of 5.41% on anhydrous wood basis.

EXAMPLE 4

A phenol-formaldehyde resol resin having code No. E-7-7-A was prepared from the phenolic-rich pyrolysis oil obtained in Example 1, by substituting such an oil for 40 wt. % of the phenol in an industrial formulation, and was used for the manufacture and evaluation of oriented strand board (OSB) panels. An industrial phenol-formaldehyde resol resin without phenol replacement and having code No. E-7-7 was also prepared for comparison.

The panel test results are shown in Table 2:

TABLE 2

| | RESIN | | OSB Panel | | | |
|---|---|---|---|---|---|---|
| Code | Phenol Replacement (wt. %) | pH | 215° C. Press Cycle (Sec.) | Density (kg/m$^3$) | Internal Bonding (MPa) | Torsion Shear (in. lb.) |
| E-7-7-A | 40 | 10.2 | 150 | 638 | 0.396 | 9.7 |
| | | | 210 | 642 | 0.515 | 23.1 |
| E-7-7 | 0 | — | 150 | 639 | 0.048 | 1.4 |
| | | | 210 | 644 | 0.446 | 14.5 |

As shown in the Table above, the mechanical properties of the panel prepared using the resin having code E-7-7-A (40% phenol replacement) are superior to those of the panel prepared using the resin having code E-7-7 (without phenol replacement).

We claim:

1. A process for the production of a phenolic-rich pyrolysis oil, which comprises the steps of:
   a) pyrolysing lignocellulosic material at a temperature of no more than about 550° C. under an absolute pressure of no more than about 50 kPa to produce pyrolysis vapors; and
   b) condensing the pyrolysis vapors to obtain a condensate consisting of a phenolic-rich pyrolysis oil having a dew point ranging from about 65 to about 75° C. under an absolute pressure of about 15 to about 20 kPa.

2. A process as claimed in claim 1, wherein said lignocellulosic material comprises bark waste.

3. A process as claimed in claim 2, wherein said bark waste is softwood bark.

4. A process as claimed in claim 3, wherein said softwood is selected from the group consisting of fir, pine, spruce, larch and mixtures thereof.

5. A process as claimed in claim 2, wherein said bark waste is in the form of particles having a particle size of about 15 to about 25 mm.

6. A process as claimed in claim 1, wherein step (a) is carried out at a temperature of about 400 to about 550° C. and an absolute pressure of about to about 50 kPa.

7. A process as claimed in claim 6, wherein said pressure ranges from about 15 to about 20 kPa.

8. A process as claimed in claim 7, wherein said temperature is about 475° C.

9. A process as claimed in claim 1, wherein the phenolic-rich pyrolysis oil obtained in step (b) has a dew point of about 68–70° C. under said absolute pressure.

10. A process as claimed in claim 1, wherein non-condensed pyrolysis vapors obtained in step (b) are further condensed at a temperature of no more than about 45° C. and an absolute pressure of about 15 to about 20 kPa to obtain a further condensate comprising an organic phase in admixture with an aqueous phase.

11. A process as claimed in claim 10, wherein said non-condensed pyrolysis vapors are further condensed at a temperature of about 15 to about 30° C.

12. A process as claimed in claim 10, wherein said organic phase is separated from said aqueous phase and the separated organic phase is subjected to an evaporation so as to recover a residue comprising a phenolic fraction boiling above 125° C. under atmospheric pressure.

13. A process as claimed in claim 12, wherein said phenolic fraction is mixed with said phenolic-rich pyrolysis oil.

14. A process as claimed in claim 13, wherein said phenolic-rich pyrolysis oil and said phenolic fraction contain high molecular weight carboxylic acids and are purified by extraction with an organic solvent selected from the group consisting of $C_5$–$C_8$ saturated hydrocarbons and petroleum ether to obtain a first fraction comprising a phenolic oil with a minor portion of said high molecular weight carboxylic acids and a second fraction comprising said organic solvent and a major portion of said high molecular weight carboxylic acids dissolved therein, said first and second fractions being immiscible with one another, separating said first and second fractions from one another and recovering the first fraction.

15. A process as claimed in claim 14, wherein said organic solvent is hexane.

16. A process as claimed in claim 1, wherein said phenolic-rich pyrolysis oil contains high molecular weight carboxylic acids and is purified by extraction with an organic solvent selected from the group consisting of $C_5$–$C_8$ saturated hydrocarbons and petroleum ether to obtain a first fraction comprising a phenolic oil with a minor portion of said high molecular weight carboxylic acids and a second fraction comprising said organic solvent and a major portion of said high molecular weight carboxylic acids dissolved therein, said first and second fractions being immiscible with one another, separating said first and second fractions from one another and recovering the first fraction.

17. A process as claimed in claim 16, wherein said organic solvent is hexane.

18. A method of purifying a phenolic-rich pyrolysis oil containing high molecular weight carboxylic acids, which comprises the steps of:
   a) extracting said oil with an organic solvent selected from the group consisting of $C_5$–$C_8$ saturated hydrocarbons and petroleum ether to obtain a first fraction comprising a phenolic oil with a minor portion of said high molecular weight carboxylic acids and a second fraction comprising said organic solvent and a major portion of said high molecular weight carboxylic acids dissolved therein, said first and second fractions being immiscible with one another;
   b) separating said first and second fractions from one another; and
   c) recovering said first fraction.

19. A method as claimed in claim 18, wherein said organic solvent is hexane.

20. A phenolic-rich pyrolysis oil derived from lignocellulosic material and having a dew point ranging from about 65 to about 75° C. under an absolute pressure of about 15 to about 20 kPa.

21. A phenolic-rich pyrolysis oil as claimed in claim 20, having a dew point of about 68–70° C. under said absolute pressure.

22. A phenolic-rich pyrolysis oil as claimed in claim 20, wherein said lignocellulosic material comprises softwood bark.

23. A method of preparing phenol-formaldehyde resol resins, which comprises substituting a phenolic-rich pyrolysis oil as defined in claim 20 for a portion of phenol in a phenol-formaldehyde resol composition.

24. A method of preparing phenol-formaldehyde resol resins, which comprises substituting a phenolic-rich pyrolysis oil as defined in claim 21 for a portion of phenol in a phenol-formaldehyde resol composition.

25. A phenol-formaldehyde resol resin containing a phenolic-rich pyrolysis oil as defined in claim 20.

26. A phenol-formaldehyde resol resin containing a phenolic-rich pyrolysis oil as defined in claim 21.

\* \* \* \* \*